United States Patent [19]
Hussein et al.

[11] Patent Number: 5,971,993
[45] Date of Patent: Oct. 26, 1999

[54] SYSTEM FOR DELIVERY OF A TRANS MYOCARDIAL DEVICE TO A HEART WALL

[75] Inventors: Hany Hussein, Costa Mesa; Stanislaw Sulek, Irvine, both of Calif.

[73] Assignee: Myocardial Stents, Inc., Costa Mesa, Calif.

[21] Appl. No.: 09/212,593

[22] Filed: Dec. 16, 1998

Related U.S. Application Data

[60] Continuation-in-part of application No. 09/098,013, Jun. 15, 1998, which is a division of application No. 08/739,724, Nov. 7, 1996, Pat. No. 5,810,836.

[51] Int. Cl.⁶ .................................................. A61F 11/00
[52] U.S. Cl. ................................................ 606/108; 623/3
[58] Field of Search ...................................... 606/108, 185, 606/215, 198; 623/11, 3, 12

[56] References Cited

U.S. PATENT DOCUMENTS

| | | | |
|---|---|---|---|
| 5,287,861 | 2/1994 | Wilk | 623/11 |
| 5,531,789 | 7/1996 | Yamazaki et al. | 623/12 |
| 5,655,548 | 8/1997 | Nelson et al. | 623/3 |

Primary Examiner—Michael Buiz
Assistant Examiner—Kevin Truong
Attorney, Agent, or Firm—James G. O'Neill

[57] ABSTRACT

A delivery device for insertion of a myocardial implant into a heart wall for trans myocardial revascularization (TMR) of the heart wall. The delivery device provides for the exact placement of one or more TMR implants into a heart wall, and has an elongated, tubular body that may include spaced-apart ports and a connecting conduit. A needle point is formed at one end to pierce the heart wall, and a handle is formed at another end to manipulate the device. The delivery device may include a surrounding sheath into which the needle point and a needle assembly may be withdrawn to release the TMR implant in the heart wall, and withdraw the delivery device from a person's body. The sheath may include a locking portion for holding the TMR implant in position when releasing the implant in a heart wall.

24 Claims, 25 Drawing Sheets

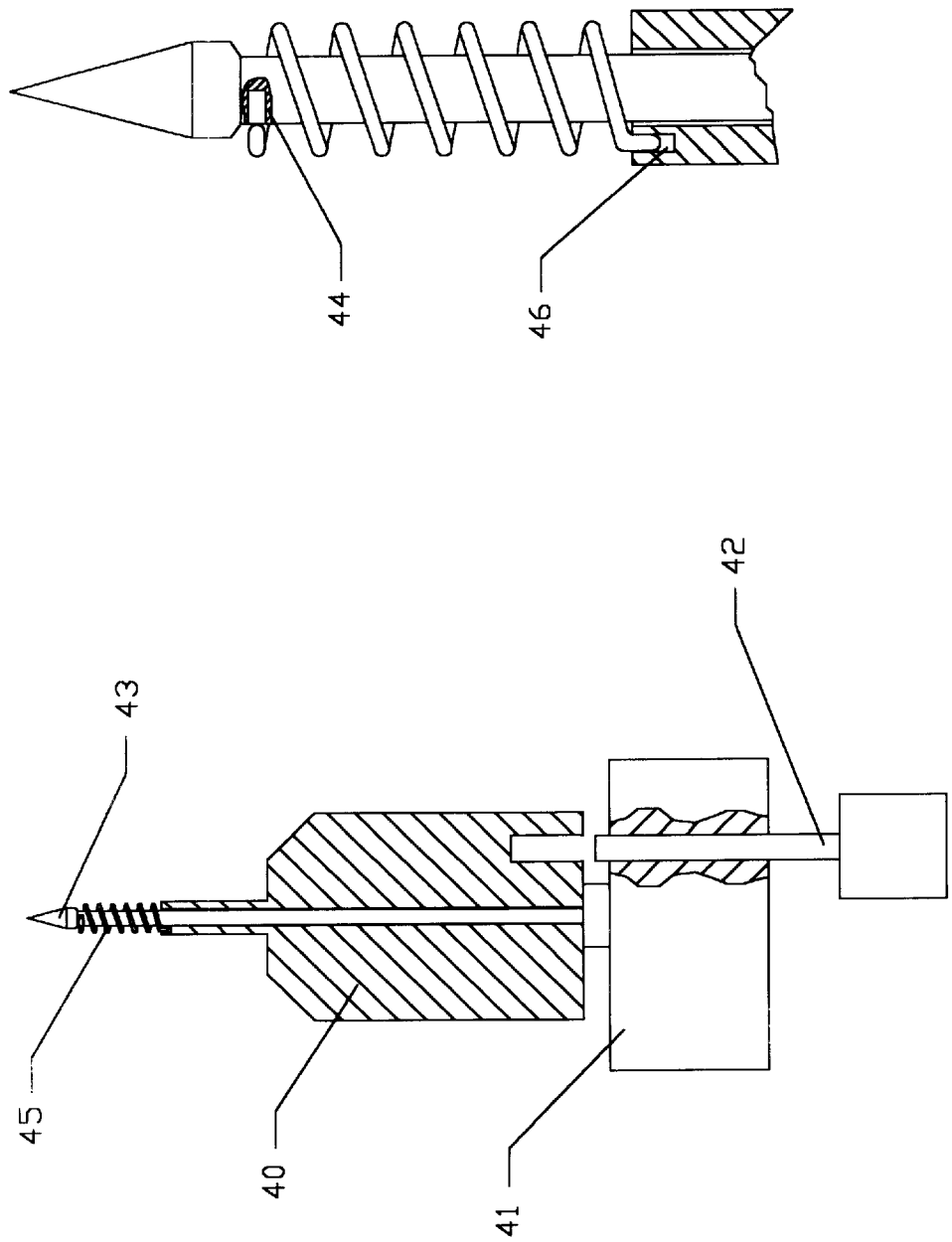

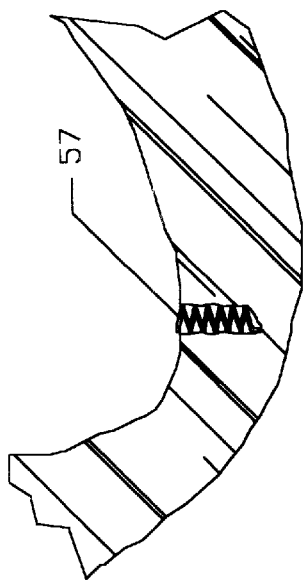
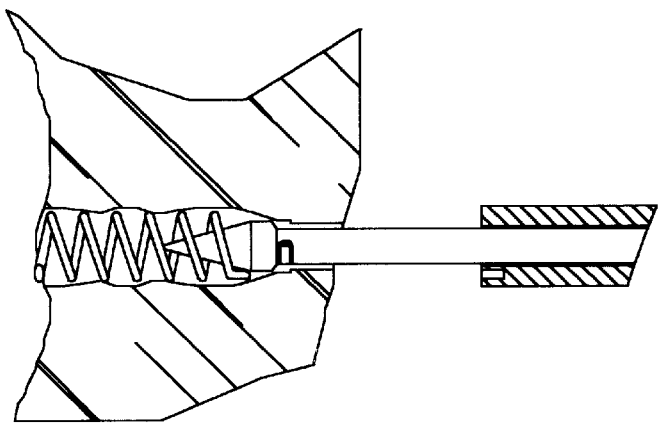
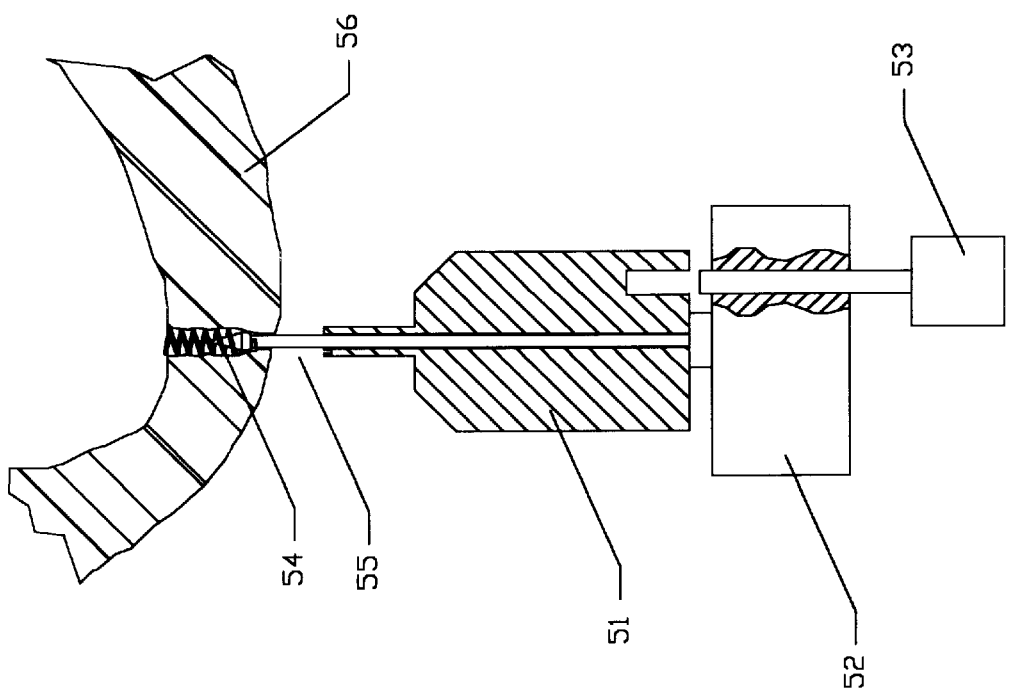

SYSTEM FOR DELIVERY OF A TRANS MYOCARDIAL DEVICE TO A HEART WALL

This is a continuation-in-part of pending application Ser. No. 09/098,013, filed Jun. 15, 1998, which is a divisional of Ser. No. 08/739,724, filed Nov. 7, 1996 now U.S. Pat. No. 5,810,836.

BACKGROUND OF THE INVENTION

1. Technical Field

This invention is generally directed to the fields of cardiac surgery and interventional cardiology, and particularly, to mechanical devices and methods suited for improving blood flow to a heart muscle by Trans Myocardial Revascularization (TMR).

2. Description of Related Art

Symptomatic occlusive coronary artery disease that does not respond to medical or interventional treatment is a major challenge for cardiac surgeons and cardiologists. The discovery of sinusoidal communications within the myocardium (Wearns, 1993) has motivated researchers to attempt various methods for myocardial revascularization based on the existence of this vascular mesh network. These methods aimed at the delivery of oxygenated blood to the vicinity of the sponge-like sinusoidal plexus in order to restore blood flow to the ischemic myocardium. Several investigators have attempted to deliver oxygenated blood directly from the left ventricle into the myocardial sinusoids by employing needle acupuncture to create transmural channels. Trans Myocardial Revascularization (TMR) has been employed clinically (Mirhoseini, 1991) by utilizing a CO2 laser for creating transmural channels in the left ventricular myocardium. These channels are typically 1 mm in diameter and extend throughout the wall thickness (15 to 20 mm) of the ventricle. It has been hypothesized that TMR works by providing a fluid conduit for oxygenated blood to flow from the endocardiac surface (heart chamber) to the mycardium inner layers thus providing oxygenated blood to myocardial cells without requiring coronary circulation; as in reptiles. Animal studies in the canine model have demonstrated the feasibility of this approach. In these studies, an increase in survival rate was demonstrated in dogs that had transmural channels and ligated coronary arteries.

While clinical studies have demonstrated improvements in patient status following TMR, histological studies indicate that the channels created for TMR tend to close shortly after the procedure. Randomized, prospective clinical trials are underway to examine the merit of TMR compared to medical treatment. In the meantime, research studies are being initiated to provide an understanding of the mechanism by which TMR actually works.

It would be desirable to develop means for maintaining the patency of TMR channels within the myocardium. Furthermore, it would be desirable to create channels for TMR without requiring the use of an expensive and bulky laser system, such as currently available CO2 laster systems. This invention provides the desired means for producing trans myocardial channels that are likely to remain patent, and that do not require laser application for generating these channels.

Specifically, the objective of the present invention is to generate needle-made channels or space in the ischemic heart wall, and to deliver or place in these channels (or space) an array of stents in order to provide improved means for supplying blood nutrients to ischemic myocardial tissue. Nutrients flow to the stented channels from the ventricular cavity, and diffuse from the side ports of the stent to the myocardial tissue through the needle-made channels. Our disclosed TMR approach of producing stented, needle-made, channels is supported by the recent scientific evidence (Whittaker et al, 1996) that needle-made transmural channels can protect ischemic tissue. Whittaker et al. assessed myocardial response at two months to laser and needle-made channels in the rat model which has little native collateral circulation. They found that channels created by a needle can protect the heart against coronary artery occlusion, and that these channels provide greater protection to ischemic tissue than channels created by laser. The limitation of needle-made channels is early closure (Pifarre, 1969). The disclosed stenting approach offers a possible solution to the early closure problem, while taking advantage of simple and effective needle-made channels for TMR.

SUMMARY OF THE INVENTION

This invention provides stent and needle means for creating and maintaining a patent lumen in the diseased myocardium. This stent provides a conduit for the flow of blood nutrients from the ventricular chamber to the intramyocardial vascular network. This stent can be used as the sole therapy or as an adjunctive therapy to other forms of TMR.

Revascularization of the myocardium can be achieved and maintained by creating stented, needle-made, channels within the myocardial tissue. These channels can allow blood nutrients within the left ventricular cavity to find direct access to ischemic zones within the ventricular wall independent of access through the coronary arteries.

Various configurations of the stent are disclosed; including flexible and rigid stents, screw stents, sleeve stents, and others. Manual or powered devices are disclosed for the delivery or placement of stents into a heart wall. The proximal end of the stent terminates at the epicardial surface and provides mechanical closure means to prevent stent detachment and leakage of blood from the ventricle. The stent is designed so as to maintain an adequate pressure gradient between the left ventricle and the myocardial tissue in order to maintain the flow from the ventricular cavity to the myocardial tissue of blood nutrients.

Furthermore, the disclosed TMR stent defines a cavity which can be pressurized during operation so as to enhance the flow of blood to myocardial tissue. Each stent can essentially operate as a mini-pump that is activated by myocardial contraction or by an external energy source.

Several embodiments of the stent and delivery systems therefor are proposed. The stents include the following: flexible spring, rigid sleeve, hollow screw, helical screw, and pumping (active) stent. The stents can be prestressed or made from memory metal in order to minimize the size of the stent during the insertion process. The various delivery systems are described below.

BRIEF DESCRIPTION OF THE DRAWINGS

FIGS. 8A–8I illustrate an alternate TMR stent and a delivery system for insertion of this TMR stent into a heart wall;

FIG. 13A is an enlarged elevational view of the distal end of the needle assembly of FIG. 12, having a myocardial implant mounted on the needle assembly;

DESCRIPTION OF PREFERRED EMBODIMENTS

The following description is provided to enable any person skilled in the art to make and use the invention, and sets forth the best modes contemplated by the inventor of carrying out his invention. Various modifications, however, will remain readily apparent to those skilled in the art, since the generic principles of the present invention have been defined herein specifically to provide an improved delivery system for stents.

Figure 1:
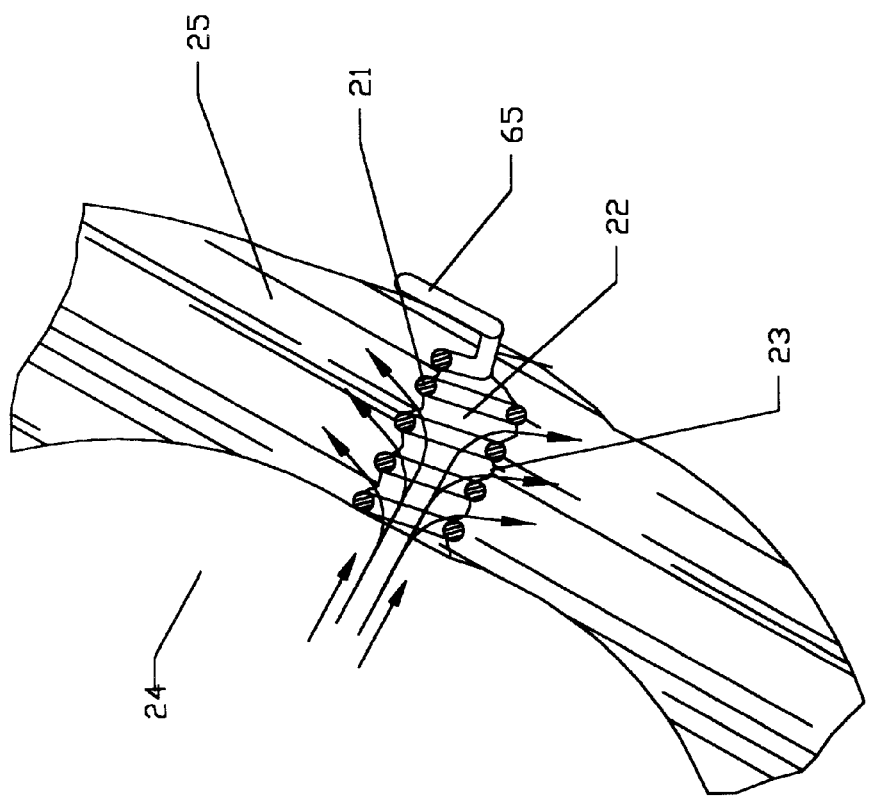
FIG. 1 is a cross-sectional view of a TMR stent inserted in a heart wall. The stent is configured as an expandable coil spring having an integral anchoring wire.

FIG. 1 shows a flexible TMR stent (hereinafter "myocardial implant") having a coil spring body 21 defining a cavity 22 and spacing 23 between the turns of said spring body. In this embodiment, blood nutrients flow from the heart chamber 24 to the heart wall 25 by passage through the coil spring cavity 22 and spacing 23. An anchoring wire 65 secures the stent to the heart wall.

Figure 2:
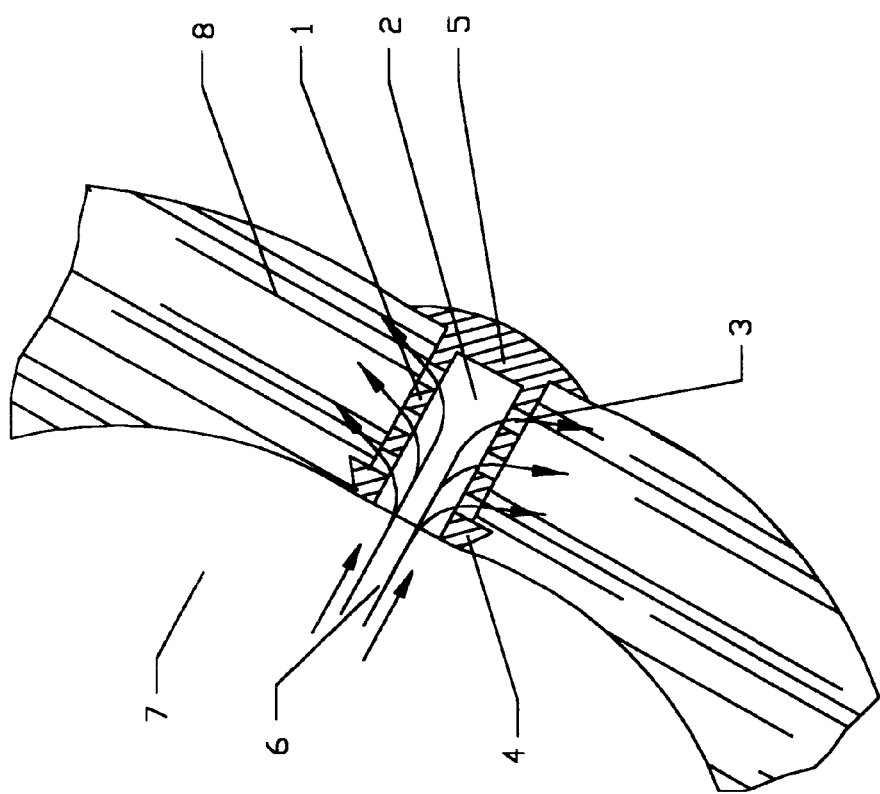
FIG. 2 is a cross-sectional view of a TMR stent having the configuration of a rigid sleeve having side ports.

FIG. 2 shows a myocardial implant that comprises a tubular body 1, cavity 2, side ports 3, retainer 4, and closure 5. In this embodiment, blood nutrients 6 are transported from the heart chamber (ventricle) 7, through the cavity 2 and side ports 3, to the heart wall 8.

Figure 3:
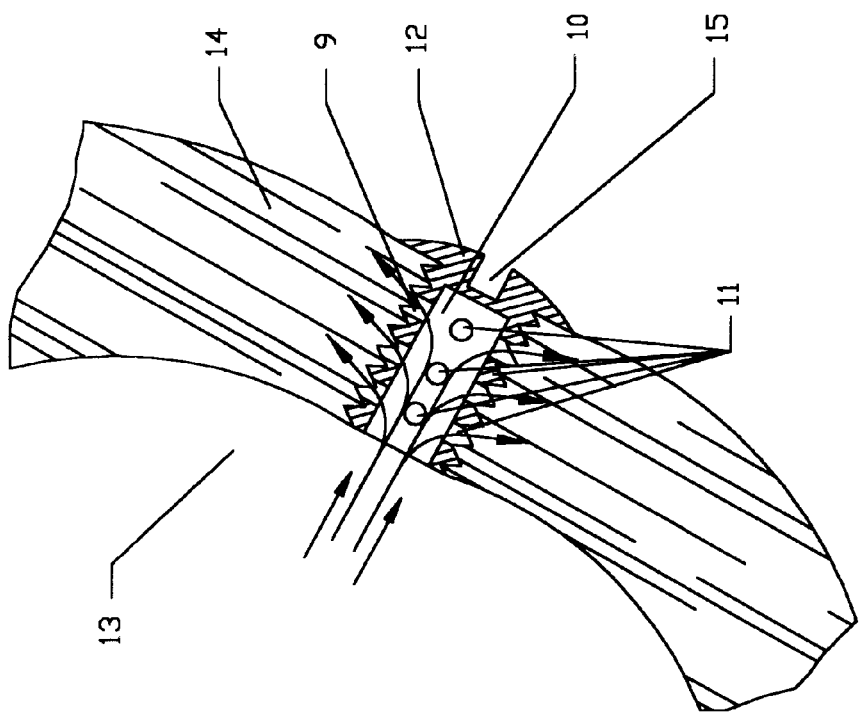
FIG. 3 is a cross-sectional view of a TMR stent having the configuration of a hollow screw with side ports.

FIG. 3 shows a myocardial implant that is configured as a hollow screw having a threaded body 9, cavity 10, side ports 11, closure 12, and slot 15. In this embodiment, blood nutrients flow from the heart chamber 13 to the heart wall 14 by passage through the cavity 10 and side ports 11.

Figure 4:
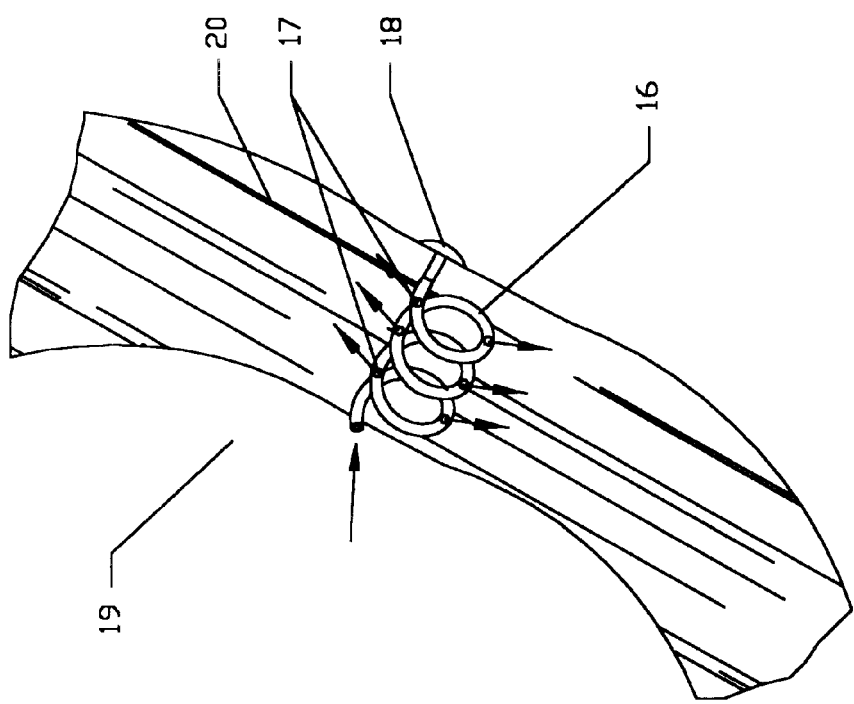
FIG. 4 is a cross-sectional view of a TMR stent having the configuration of a wire screw.

FIG. 4 shows a myocardial implant that is a hollow wire screw having an elongated hollow coil body 16, side ports 17, and anchor 18. In this embodiment, blood nutrients flow from the heart chamber 19 to the heart wall 20 by passage through the hollow core of the wire 16 and side ports 17.

Figure 5:
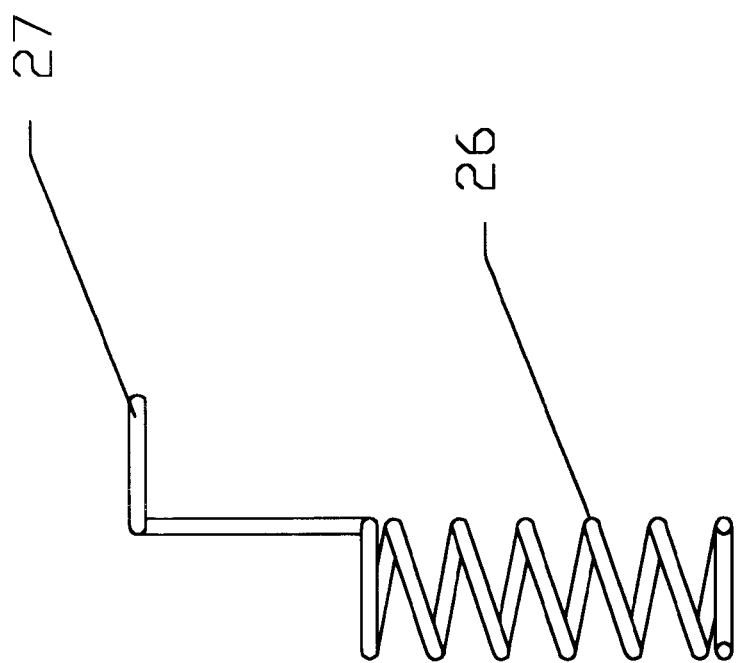
FIG. 5 is a cross sectional view of a flexible stent having an integral anchoring coil.

FIG. 5 shows a flexible myocardial implant having a coil body 26 and an anchoring coil 27 which is an integral part of the myocardial implant. The anchoring coil prevents detachment of the myocardial implant from the heart wall.

Figure 6:
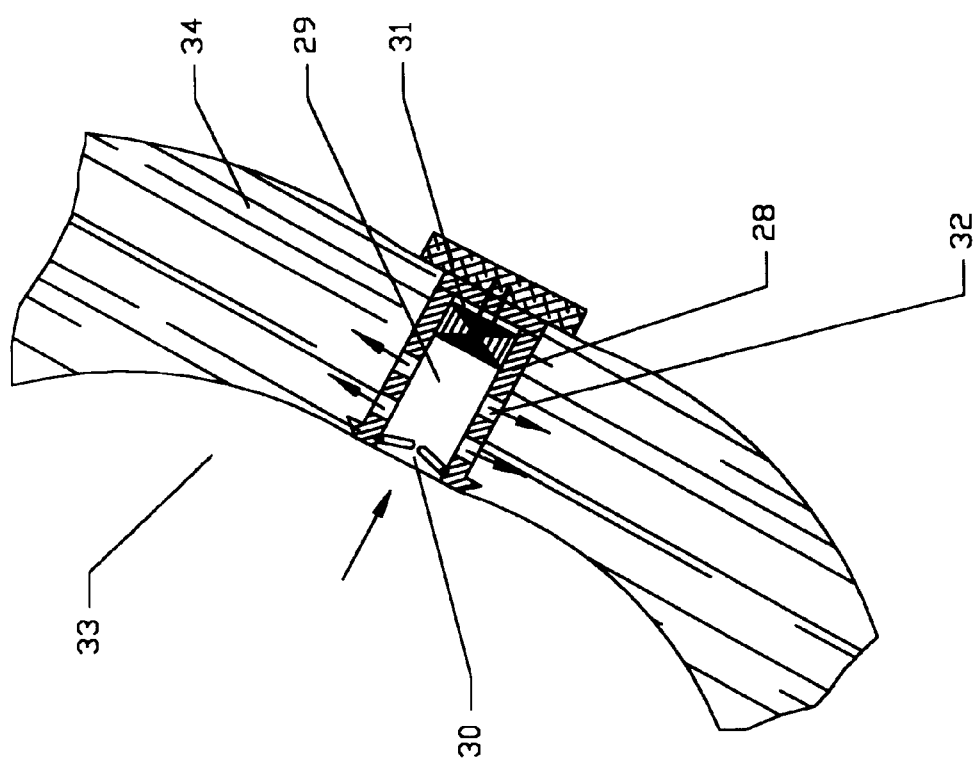
FIG. 6 is a cross-sectional view of a TMR stent having the configuration of a miniature pump.

FIG. 6 shows a myocardial implant having a cylindrical body 28 defining a cavity 29. A valve 30, pumping element 31, and side ports 32 are situated within the cavity 29. In this embodiment, blood nutrients flow from the heart chamber 33 to the pumping cavity 29. The valve 30 is activated and the pumping element 31 operates to displace the blood from the pumping cavity 29 through side ports 32 to the heart wall 34.

Figure 7:
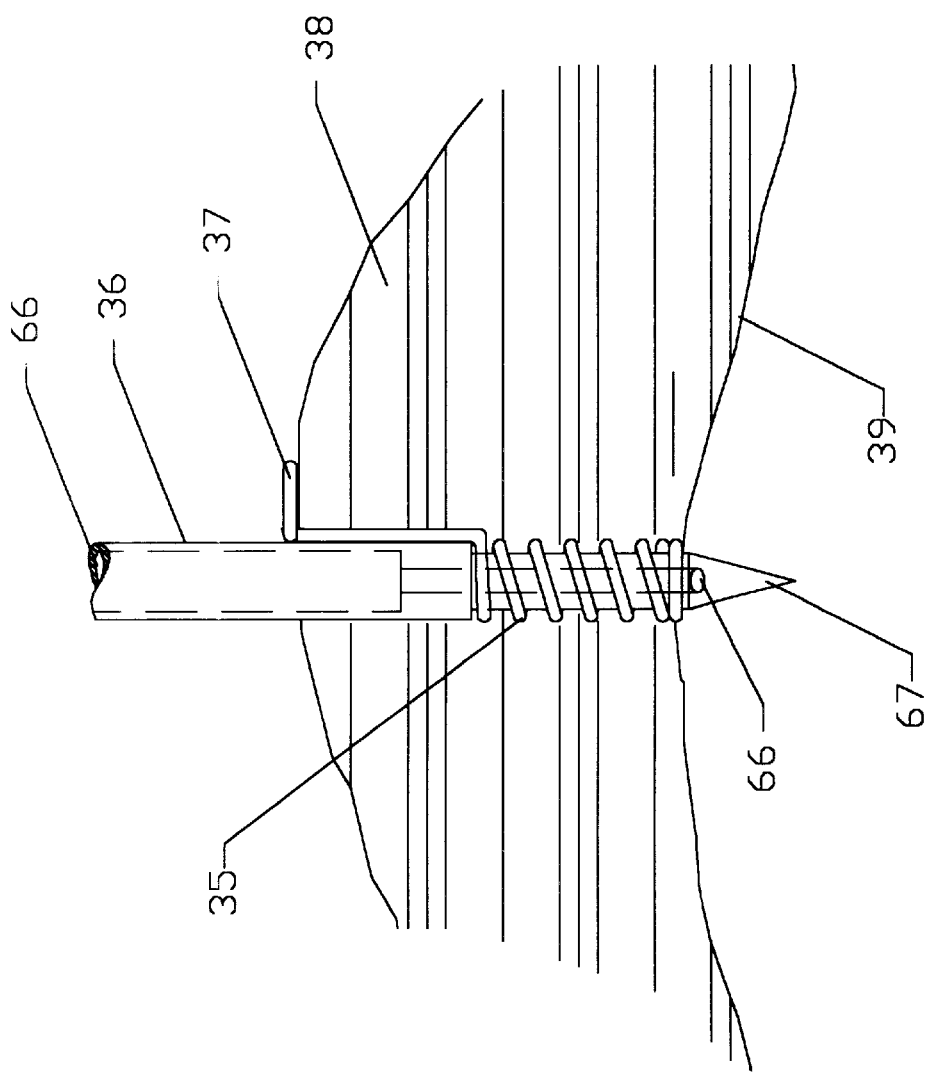
FIG. 7 shows a TMR delivery device and method for insertion of a TMR stent into a heart wall.

FIG. 7 shows the construction and method of use of one embodiment of a delivery device for creating a pathway in the heart wall and for placement of a myocardial implant in this pathway. In this first embodiment, a needle obturator 36 carries a myocardial implant 35 having an anchoring wire 37, which may be offset from the myocardial implant, as shown in FIG. 7, or aligned with the myocardial implant, as shown in FIGS. 18A–22. The obturator and myocardial implant are inserted through the heart wall 38 until the endocardiac surface is reached. After the endocardiac surface 39 of the heart wall is reached, the obturator 36 is removed, as by turning or unscrewing the same, thereby leaving the myocardial implant 35 embedded in the heart wall. Additional improvements include a fluid channel 66 that is formed in the obturator body to provide an indication that the obturator's distal end 67 has crossed the endocardiac surface 39.

Figure 8D:
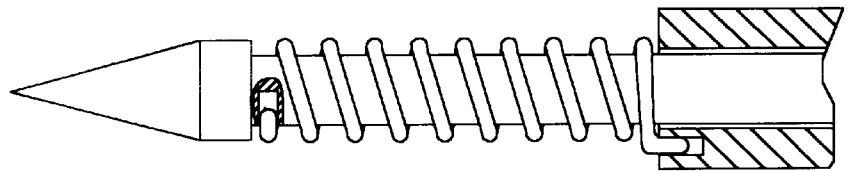

FIGS. 8A through 8I show the construction of an alternate myocardial implant and a second embodiment of a delivery system for placement of the alternate implant in a heart wall. FIG. 8A shows a delivery system having a pin 40 and handle 41 having a locking device 42. An obturator 43 is mounted in the pin 40. The obturator 43 has a recess 44 (FIG. 8B) to engage the distal end of a myocardial implant 45. The pin 40 has a recess 46 (FIG. 8B) to engage the proximal end of the implant 45.

Figure 8C:
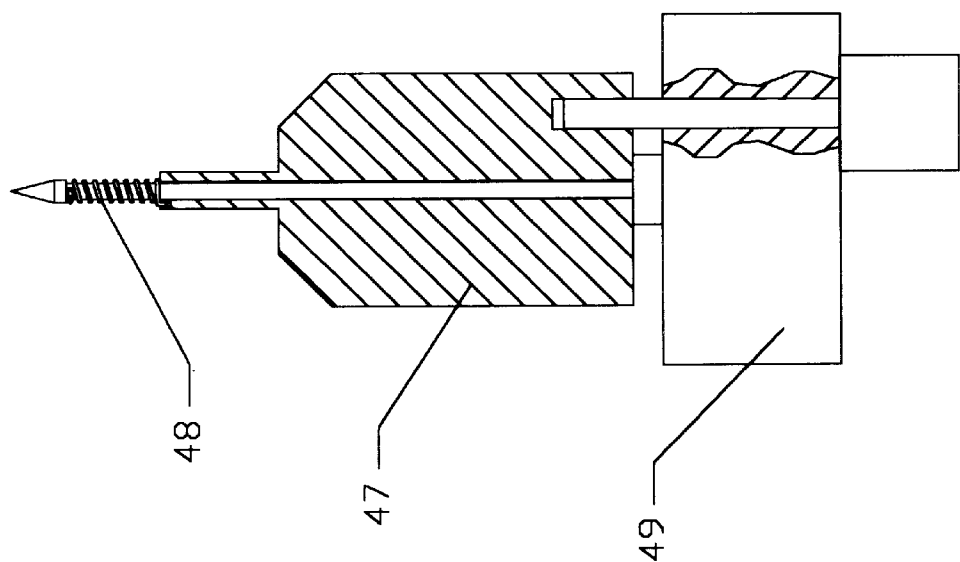
Figure 8F:
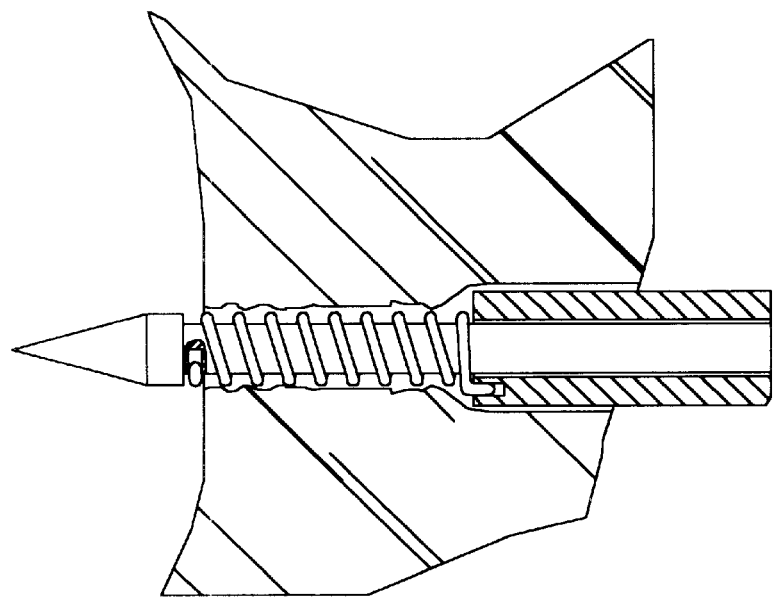
Figure 8E:
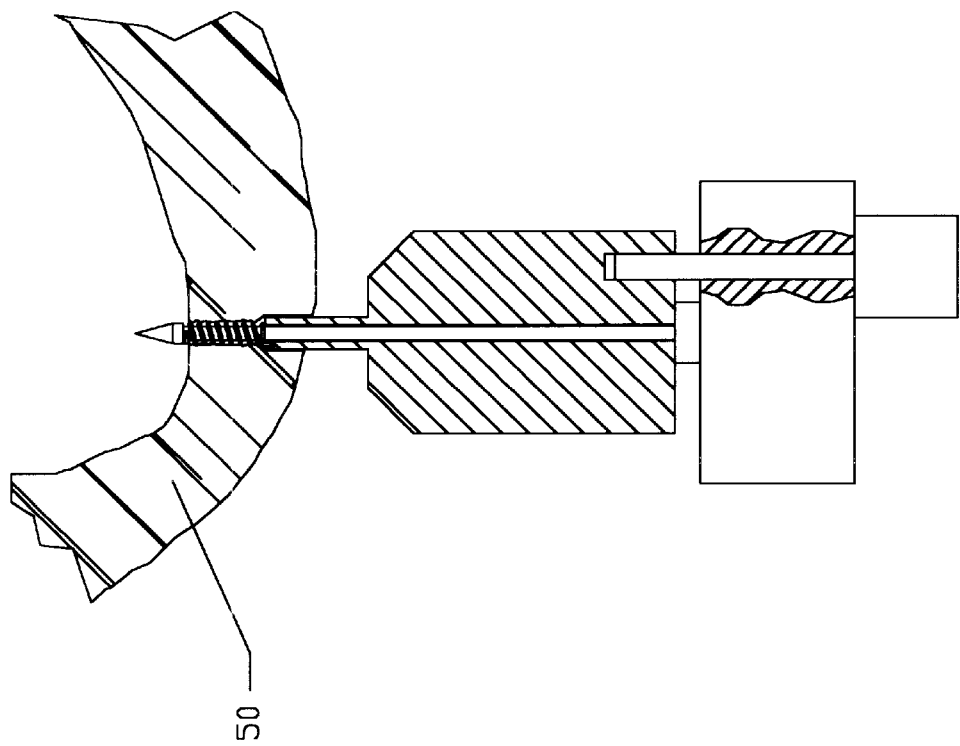

The method of use involves the placement of the implant 45 over an obturator 43. The pin 40 is then rotated to create a radial stress on the TMR device 45 (FIG. 8D). The pin 40 is locked to the handle 41 (FIG. 8C). Advancement through the heart wall 50 of the obturator and TMR device 45 is achieved by pressing the obturator through the heart wall (FIGS. 8E, 8F). The pin 40 is released from handle 41 by withdrawing the locking device 42 (FIGS. 8G, 8H). This causes the implant 45 to be released from the obturator 43. The obturator 43 is then pulled back from the heart wall 50 leaving the implant 45 imbedded in the heart wall (FIG. 8I).

Figure 9:
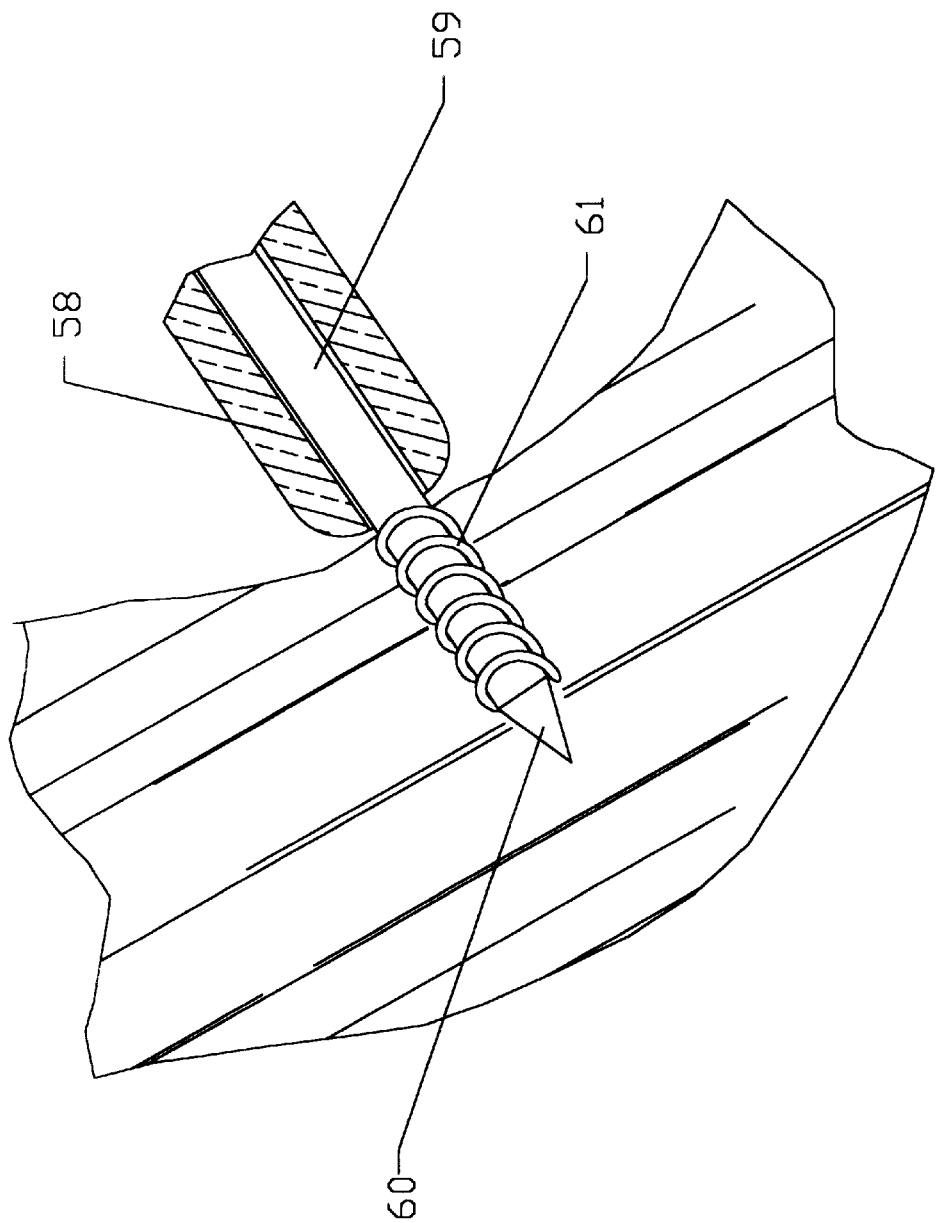
FIG. 9 shows a catheter delivery device and method utilizing a percutaneous access for insertion of a TMR stent into a needle-made space within the heart wall.

FIG. 9 shows a catheter 58 having a slidable wire 59 which terminates at its distal end in a needle point 60. A myocardial implant 61 is mounted proximal to the needle point. Advancing the needle spreads the heart wall tissue and positions the implant 61 into that tissue. Withdrawal of the needle releases the implant 61 in the heart wall.

Figure 10:
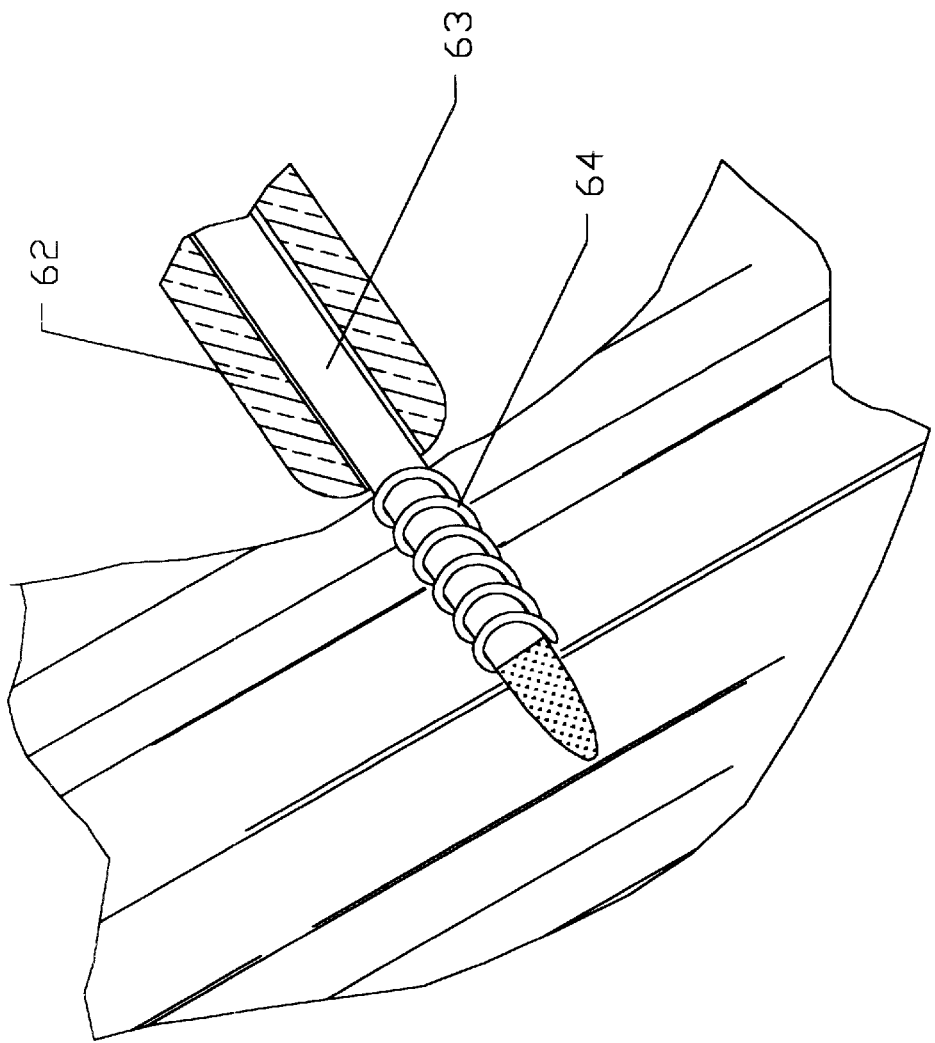
FIG. 10 shows an alternate catheter delivery device and method utilizing a percutaneous access for creating a channel in the heart wall, and for insertion in this channel of a TMR stent.

FIG. 10 shows a catheter 62 which incorporates a slidable wire 63 that terminates at its distal end into a drill or other mechanical attachment 65 for making holes in the heart wall tissue. A myocardial implant 64 is mounted proximal to the drill 65 on the slidable wire 63. Advancing the drilling tool creates a channel in the tissue and positions the implant 64 in this channel. Withdrawal of the drilling tool releases the implant 64 in the heart wall.

The disclosed myocardial implants are expected to incorporate a cavity having a diameter in the range of 1–5 millimeters and a length in the range of 10–30 millimeters. The bodies of the myocardial implants are made of a bio-compatible material; such as stainless steel. The myocardial implants may also be coated with a material that promotes angiogenesis (formation of new blood vessels). The myocardial implants may also be made from carbon, gold, platinum, or other suitable materials.

The number of myocardial implants required of used for each patient depends on the size of the implants and the surface area of the heart segment that is being revascularized. For example, a small segment may require only one myocardial implant, while a large segment may require 10 implants to be implanted in the heart wall.

Turning now to FIGS. 11–22, there shown are alternate embodiments of delivery systems for implanting myocardial implants in a heart wall.

Figure 11:
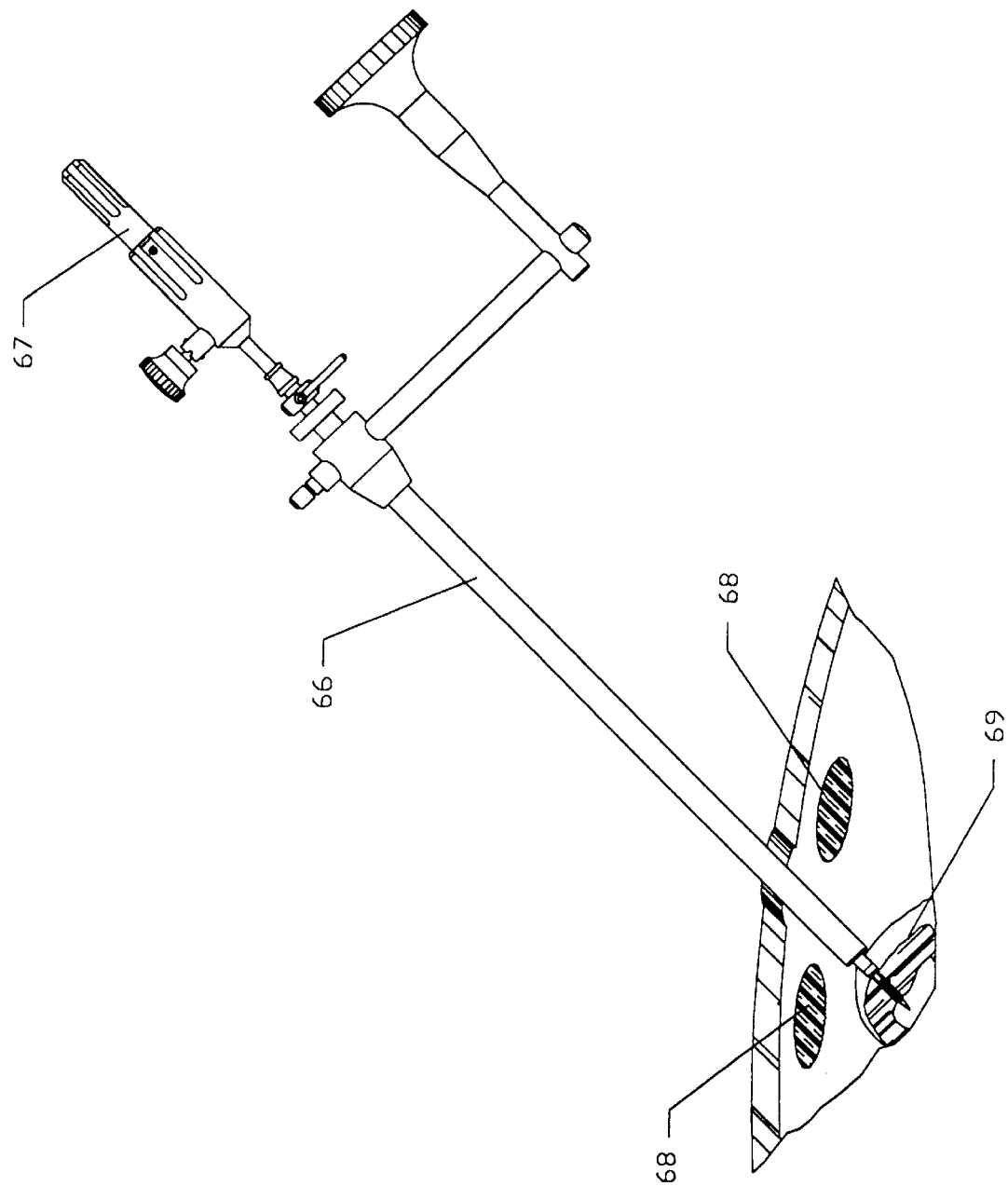
FIG. 11 is a front elevational view of a system for delivery to a heart wall of an implant (myocardial stent)

FIG. 11 illustrates a system for the delivery to a heart wall of a myocardial implant. This system consists of a thoracoscope 66 and an obturator assembly 67. The thoracoscope provides means for optical guidance in order to permit minimally-invasive access to the heart wall. The system allows penetration of the chest wall of a patient between ribs 68, to allow the obturator assembly 67 to penetrate the heart wall 69, and leave the implant in the heart wall.

Figure 12:
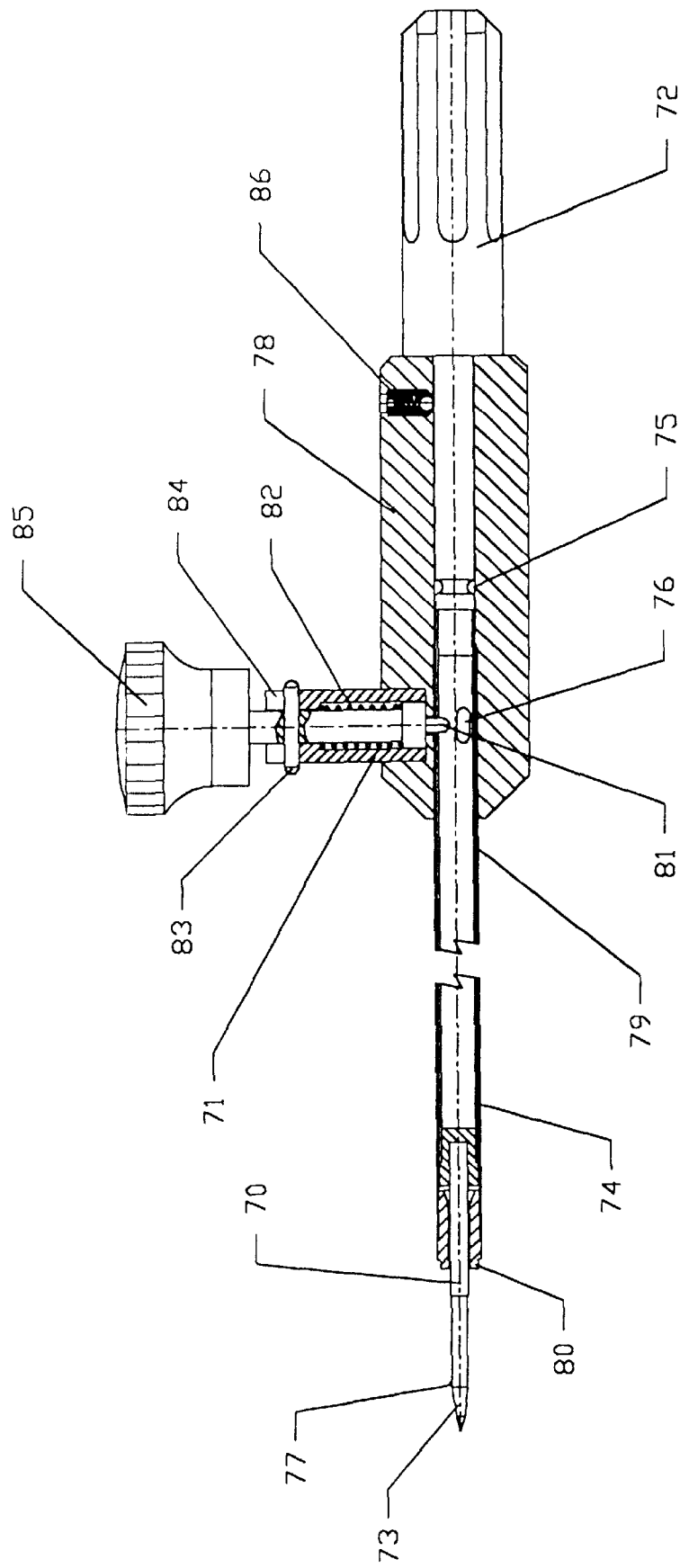
FIG. 12 is a front elevational view, partly in cross section, of an obturator assembly having a needle assembly and sheath assembly.

FIG. 12 shows an enlarged cross section of a preferred embodiment of an obturator assembly, such as 67, having a needle assembly 70 and a sheath assembly 71. The needle assembly 70 contains, at its proximal end a handle 72, and at its distal end, a needle tip 73. A needle shaft 74 connects the proximal and distal of the needle assembly 70. The needle shaft contains a groove 75 and a plurality of holes or openings 76 to removably couple the needle shaft to the outer sheath assembly 71 during use. A pin 77 is mounted proximal to needle tip 73 in order to support a myocardial implant, and to permit the implant to be threaded into heart wall tissue. The sheath assembly 71 contains, at its proximal end, a handle 78 that is connected to tubing 79. The distal end of the tubing 79 is shaped to form a key or holding portion 80 that provides means for locking the myocardial implant onto the sheath. A further holding element or pin 81 provides means for coupling the sheath assembly to the needle assembly. A spring 82 supports the pin 81 and a stop 83 provides means to hold the pin 81 in place. A slot 84 provides means to place pin 81 in a locking during use. A pin 77 is mounted proximal to needle tip 73 in order to support a myocardial implant, and to permit the implant to be threaded into heart wall tissue. The sheath assembly 71 contains, at its proximal end, a handle 78 that is connected to tubing 79. The distal end of the tubing 79 is shaped to form a key or holding portion 80 that provides means for locking the myocardial implant onto the sheath. A further holding element or pin 81 provides means for coupling the sheath assembly to the needle assembly. A spring 82 supports the pin 81 and a stop 83 provides means to hold the pin 81 in place. A slot 84 provides means to place pin 81 in a locking position. A spring-loaded pin 86 provides means to engage or lock the needle assembly 70 to the sheath assembly 71, during removal of the obturator assembly 67 from a human body.

FIG. 13A is an enlarged view of the distal end of a needle assembly, such as 70, having a myocardial implant 87 mounted on the needle assembly. The proximal end of the implant is secured onto the sheath assembly, with the key 80 locking or holding a portion 88 of the implant, to prevent rotation of the implant during insertion and withdrawal of needle assembly from a heart wall.

Figure 13:
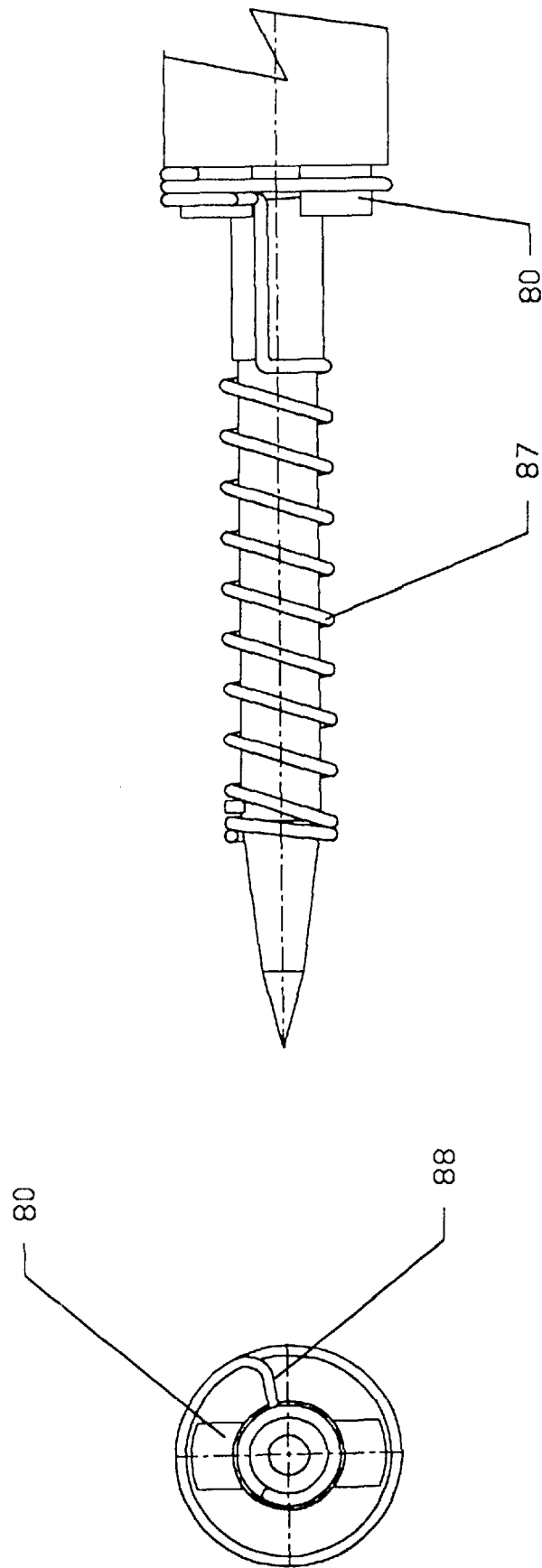
FIG. 13 is a left end view of FIG. 13A.

FIG. 13 is a left end view of FIG. 13A, and shows the implant 87 secured to the key 80 by the locking portion 88 of the implant.

Figure 14:
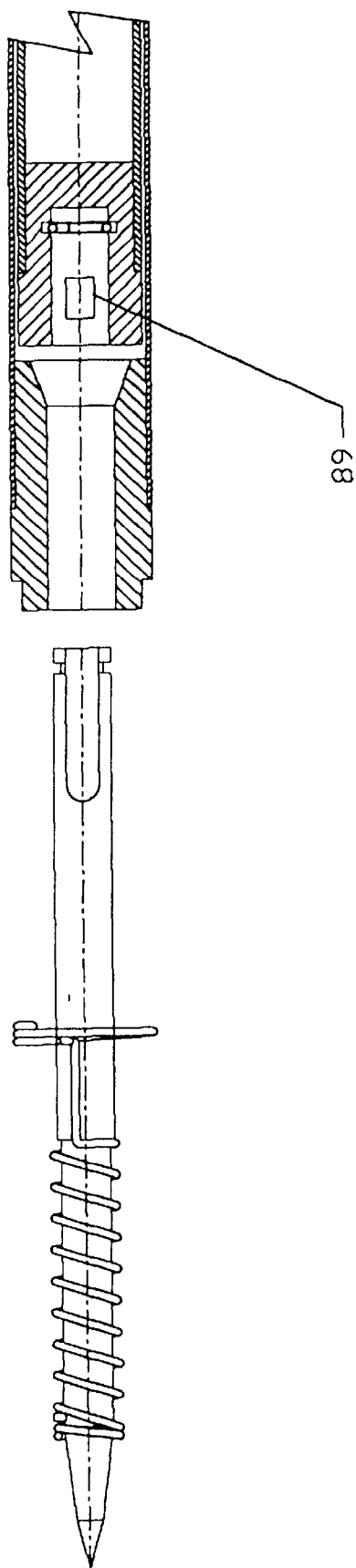
FIG. 14 is a side elevational view, partly in cross section, of an alternate embodiment of a needle assembly.

FIG. 14 shows a further embodiment of a delivery system, having a modified needle assembly. In this configuration, the distal end of the needle assembly is made detachable from the rest of the assembly, as by means of a mechanical coupling 89.

Figure 15:
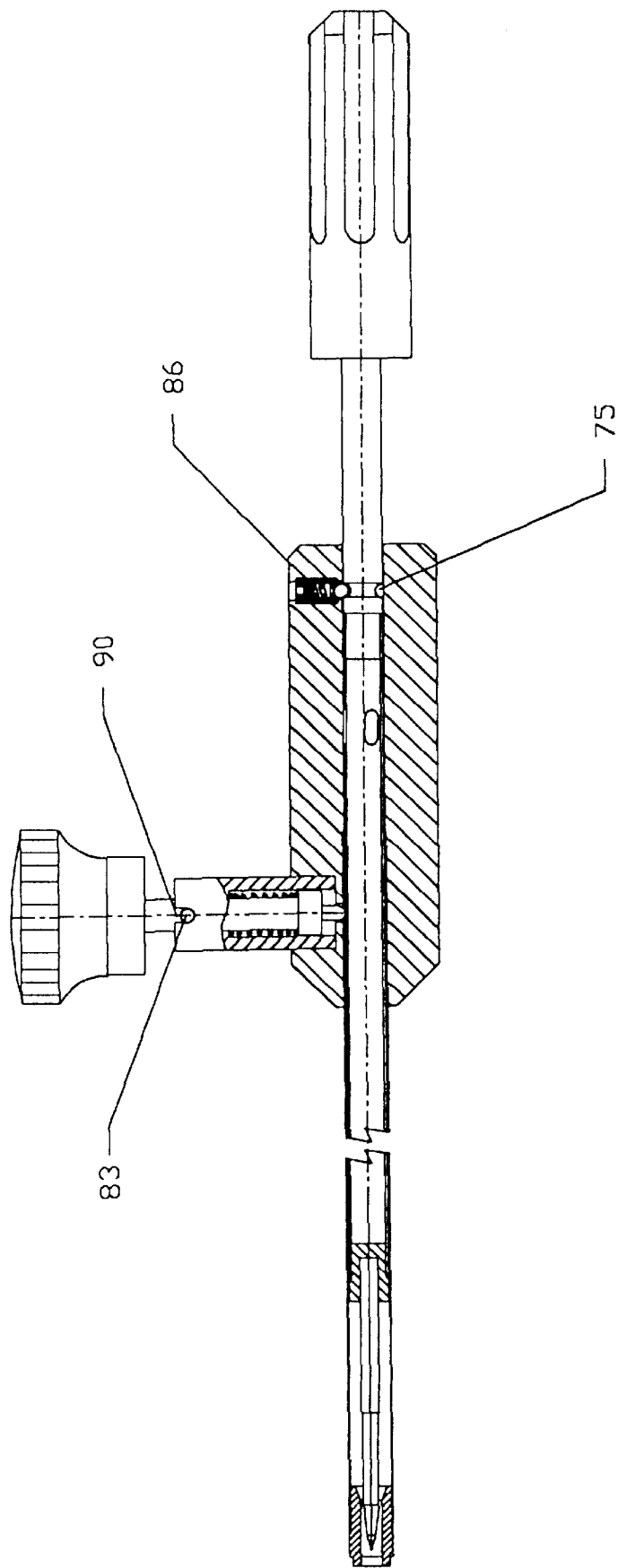
FIG. 15 is a front elevational view of the obturator assembly of FIG. 12, in position for removal from a heart wall following delivery of an implant.

FIG. 15 is a further cross section of the obturator assembly shown in FIG. 12, with the needle assembly in a retracted position for removal from a heart wall, following delivery of an implant. In this retracted position, the locking pin 83 is seated in a groove 90, and the spring-loaded pin 86 is engaged in groove 75.

Referring now to FIGS. 16–22, there shown is yet another embodiment of the delivery system of the present invention.

Figure 16:
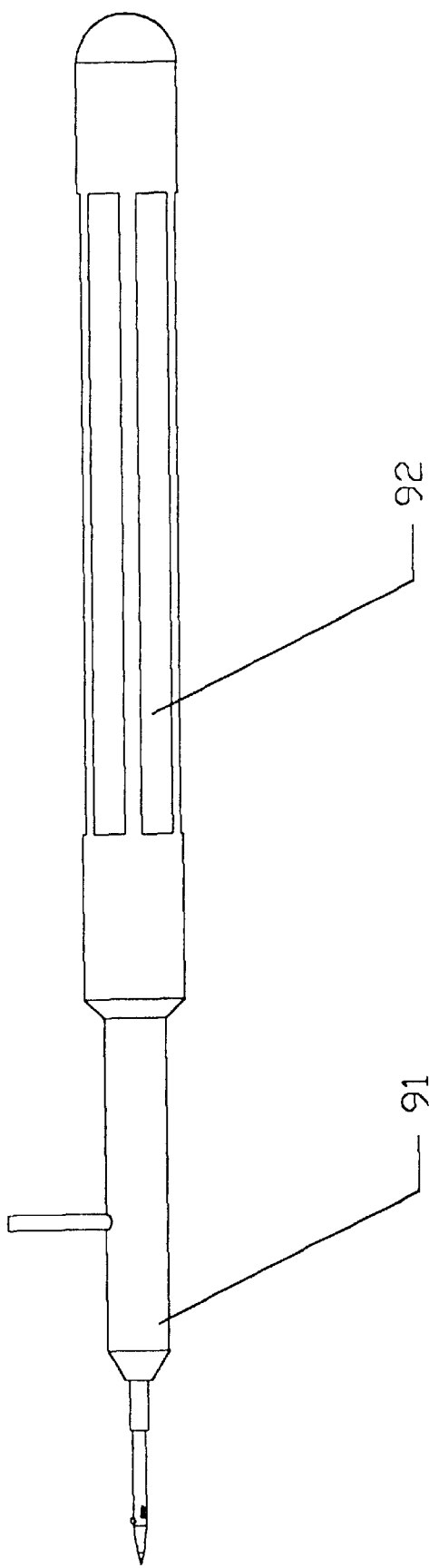
FIG. 16 is a front elevational view of a further embodiment of an obturator for delivery of an implant to a heart wall.

FIG. 16 shows a delivery device (obturator) 91, having a distal end and a proximal end 92, for delivery of an implant to a heart wall.

Figure 17:
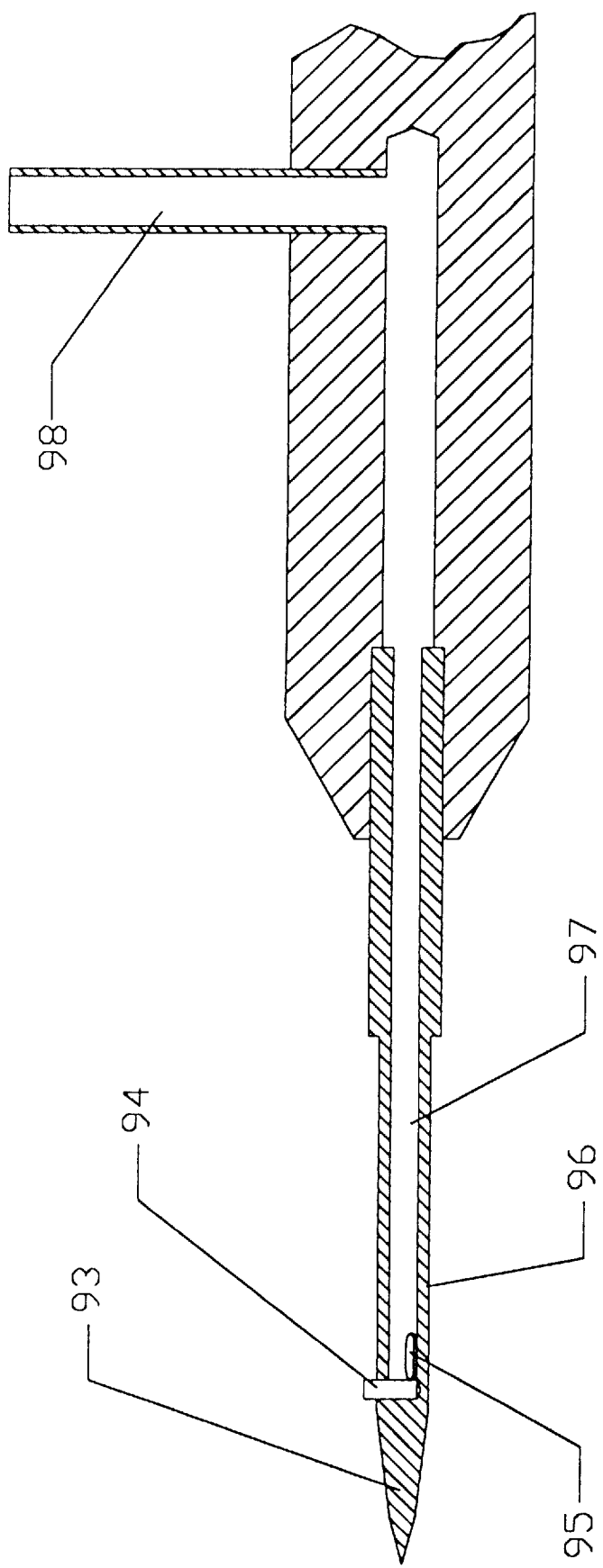
FIG. 17 is an enlarged, partial cross sectional view of the needle end of the device shown in FIG. 16.

FIG. 17 is an enlarged cross section of the distal end of the obturator device 91, shown in FIG. 16. This device includes a needle assembly 96, having a needle tip 93, used to puncture tissue, a pin 94 used to thread and support an implant, a port 95, which is in fluid communication with an internal conduit 97 and an indicator tube 98. The port 95 allows blood inside a heart to enter internal conduit 97 and to exit though an internal conduit indicator tube 98, in order to demonstrate complete penetration of the heart wall by the obturator.

Figure 18B:
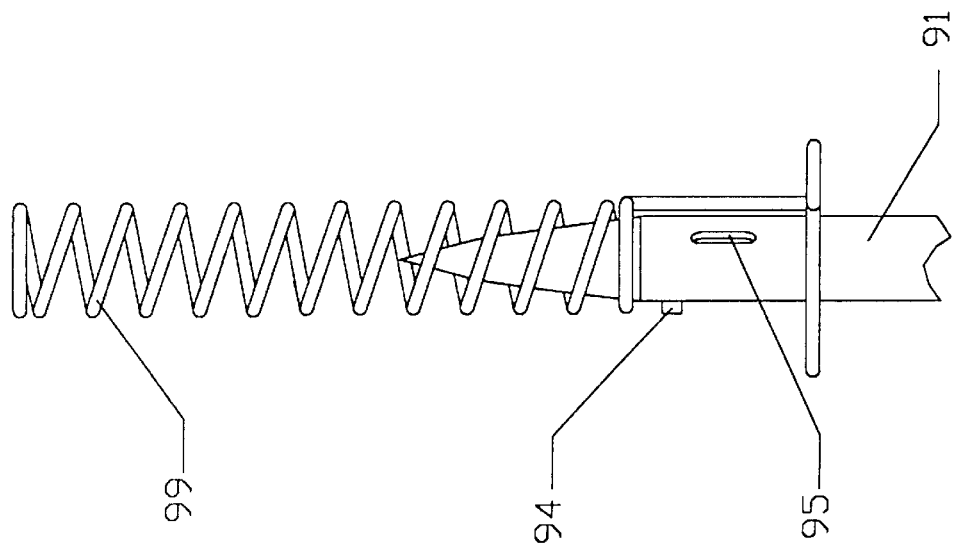
FIG. 18B is an enlarged elevational view of the mycardial implant and needle end of FIG. 18A.
Figure 18A:
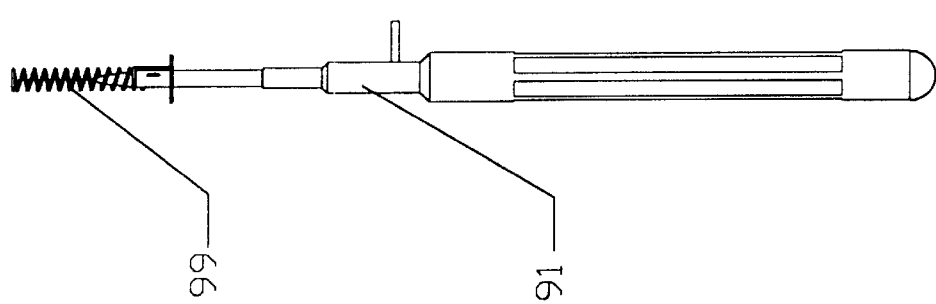
FIG. 18A is a further front elevational view of the obturator shown in FIG. 16, with a myocardial implant partially mounted on the needle end.

FIG. 18A shows a myocardial implant 99 partially mounted on the distal end of the obturator 91, while FIG. 18B shows an enlarged view of the myocardial implant 99 and the distal end of the obturator 91. As discussed above, the pin 94 engages the implant 99 opposite from the port 95.

Figure 19:
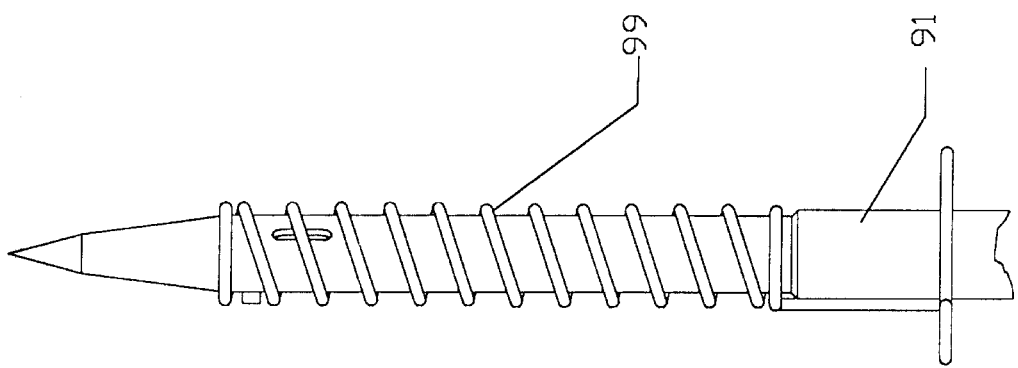
FIG. 19 is an enlarged elevational view showing the myocardial implant of FIG. 18B, completely mounted on the needle end.

FIG. 19 shows the myocardial implant 99 completely mounted on the distal end of the obturator 91, in position for insertion into a heart wall.

Figure 20:
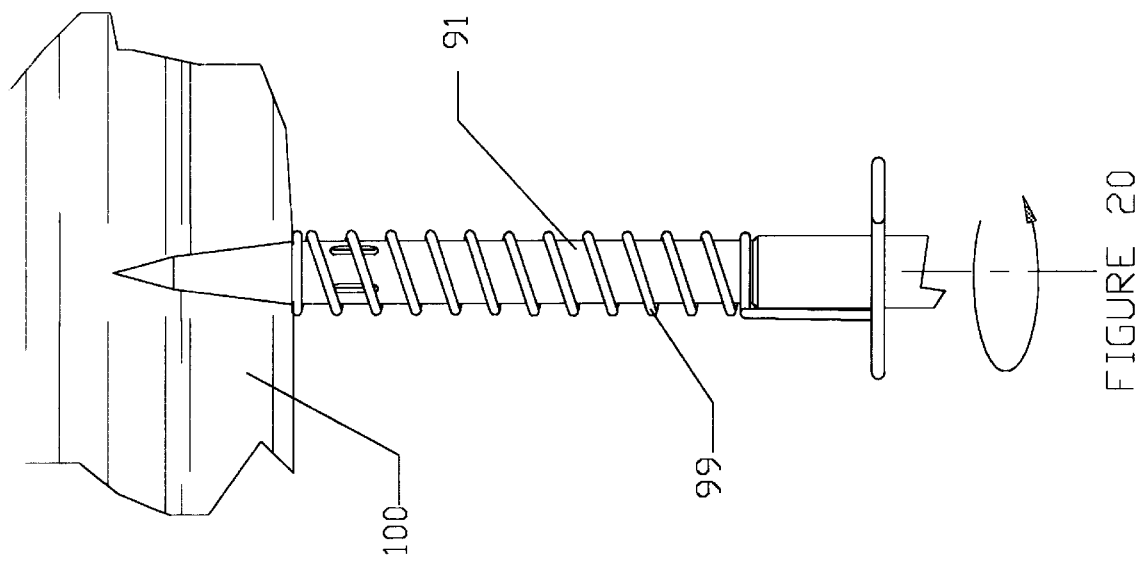
FIG. 20 is a further elevational view of the myocardial implant completely mounted on the needle end being inserted in a heart wall by rotation of the obturator.

FIG. 20 illustrates how the myocardial implant 99 is inserted into a heart wall 100 by rotation of the obturator 91.

Figure 21:
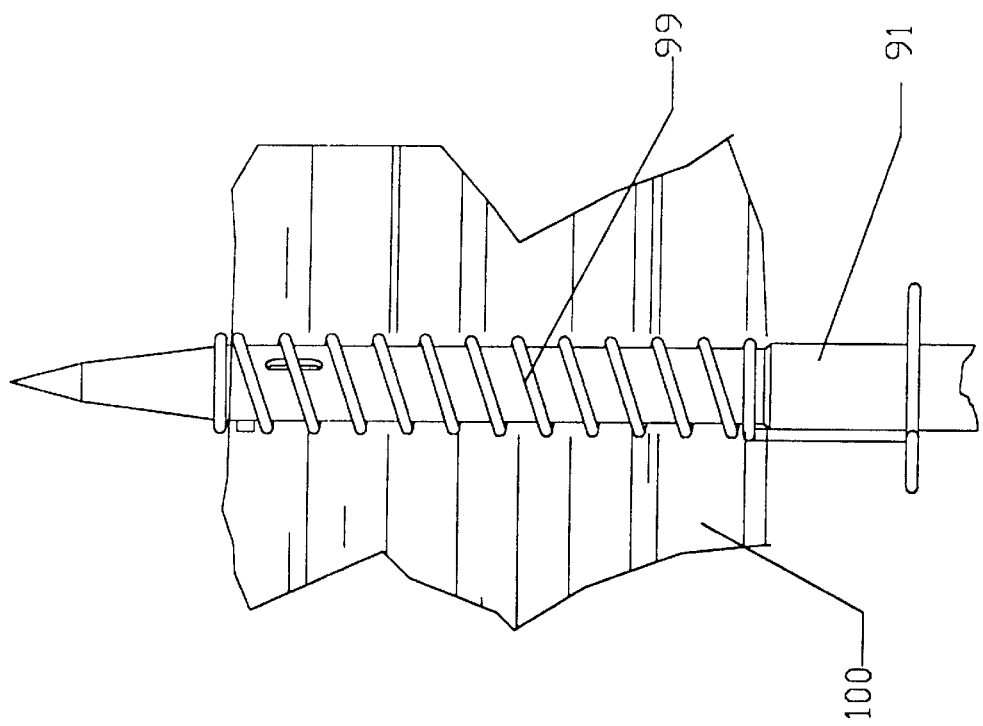
FIG. 21 shows the obturator and myocardial implant fully inserted into the heart wall.

FIG. 21 illustrates the implant 99 inserted completely into the heart wall 100, while it is still held on the obturator 91.

Figure 22:
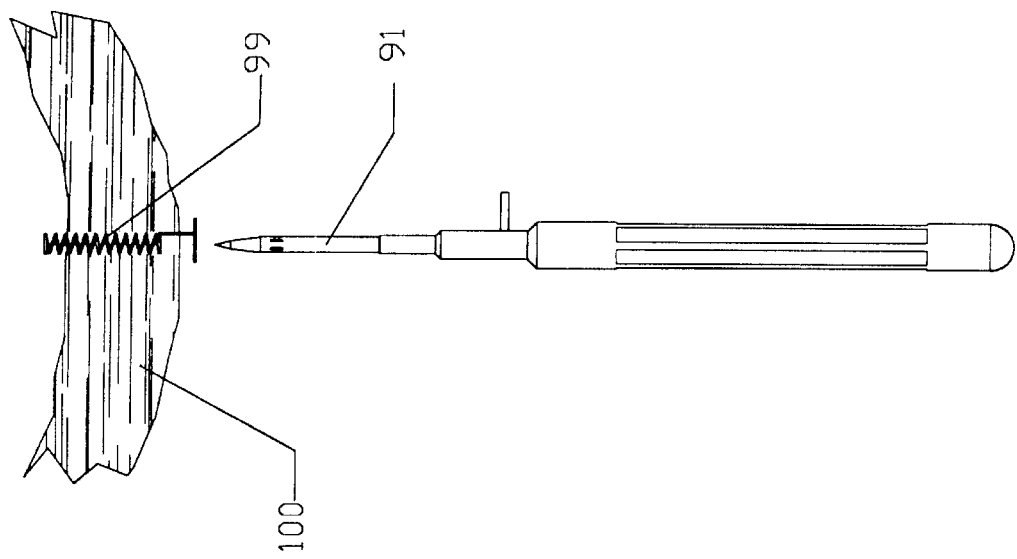
FIG. 22 shows the obturator removed from the heart wall with the implant left in the heart wall.

Finally, FIG. 22 shows the implant 99 inserted into the heart wall 100, with the obturator 91 withdrawn.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other

What is claimed is:

1. A delivery system for delivery to and insertion in a heart wall of a separate trans myocardial revascularization (TMR) implant; the delivery system comprising, in combination:

an elongated, tubular body to carry and insert the TMR implant into the heart wall;

the elongated, tubular body having a distal end and a proximal end;

a needle point formed on the distal end;

the TMR implant carried on the distal end of the elongated, tubular body, adjacent the needle point;

a pin mounted on the distal end of the elongated, tubular body, adjacent the needle point, to hold the TMR implant during insertion into the heart wall; and a handle formed on the proximal end for rotation of the elongated, tubular body when inserting the TMR implant into the heart wall.

2. The delivery system of claim 1 wherein the needle point is connected to a needle shaft and a sheath assembly surrounds the needle shaft.

3. The delivery system of claim 2, further including means for releasably coupling the sheath assembly to a proximal end of the TMR implant.

4. The delivery system of claim 3 wherein the means for releasably coupling the sheath assembly to the TMR implant is a mechanical device.

5. The delivery system of claim 2, further including means for releasably coupling the sheath assembly to the needle shaft during insertion of the TMR implant into the heart wall.

6. The delivery system of claim 5, further including means for releasably coupling the sheath assembly to the needle shaft during withdrawal of the delivery system from a human body.

7. The delivery system of claim 5 wherein the means for releasably coupling the sheath assembly to the needle shaft is a retractable pin.

8. The delivery system of claim 7, further including a handle for locking or unlocking the retractable pin.

9. The delivery system of claim 8, further including a plurality of openings formed in the needle shaft, which plurality of openings are selectively cooperable with the retractable pin to releasably couple the sheath assembly to the needle shaft.

10. The delivery system of claim 5 wherein the needle shaft is removably held in a needle assembly.

11. The delivery system of claim 1, further including an internal conduit formed in the elongated, tubular body, which internal conduit is in fluid communication between a port formed in a needle shaft connected to the needle point and an indicator port formed adjacent the distal end.

12. A delivery system for delivery to and insertion in a heart wall of a separate trans myocardial revascularization (TMR) implant; the delivery system comprising;

an elongated, tubular body to carry and insert the TMR implant into the heart wall;

the elongated body having a distal end and a proximal end;

a needle shaft having a needle point formed on the distal end;

the TMR implant carried on the needle shaft;

a pin mounted on the needle shaft to support the TMR implant during insertion into the heart wall;

a handle formed on the proximal end for rotation of the elongated, tubular body when inserting the TMR implant into the heart wall;

a port formed in the needle shaft;

an indicator port formed adjacent the distal end; and an internal conduit formed between the port and the indicator port to allow fluid communication there between.

13. The delivery system of claim 12 wherein the handle is comprised of a gripping portion and a stepped down portion, connected to the needle shaft, and the indicator port is formed on the stepped down portion.

14. The delivery system for delivery to and insertion in a heart wall of a separate trans myocardial revascularization (TMR) implant; the delivery system comprising, in combination:

an elongated, tubular body to carry and insert the TMR implant into the heart wall;

the elongated, tubular body having a distal end and a proximal end;

a needle point formed on the distal end;

the TMR implant carried on the distal end of the elongated, tubular body, adjacent the needle point;

a pin mounted on the distal end of the elongated, tubular body, adjacent the needle point, to hold the TMR implant during insertion into the heart wall;

a handle formed on the proximal end for rotation of the elongated, tubular body when inserting the TMR implant into the heart wall; and a sheath assembly surrounding the needle shaft.

15. The delivery system of claim 14, further including means for releasably coupling the sheath assembly to a proximal end of the TMR implant.

16. The delivery system of claim 15 wherein the means for releasably coupling the sheath assembly to the TMR implant is a mechanical device.

17. The delivery system of claim 14, including further means for releasably coupling the sheath assembly to the needle shaft.

18. The delivery system of claim 17, further including further means for releasably coupling the sheath assembly to the needle shaft during withdrawal of the delivery system from a human body.

19. The delivery system of claim 18 wherein the means for releasably coupling the sheath assembly to the needle shaft is a retractable pin.

20. The delivery system of claim 19, further including a handle for locking or unlocking the retractable pin.

21. The delivery system of claim 20, further including a plurality of openings formed in the needle shaft, which plurality of openings are selectively cooperable with the retractable pin to releasably couple the sheath assembly to the needle shaft.

22. The delivery system of claim 21 wherein the needle shaft is removably held in a needle assembly.

23. The delivery system of claim 14 wherein the handle may be pulled in a direction, away from the distal end to withdraw the needle shaft and needle point into the sheath assembly.

24. The delivery system of claim 23, further including a releasable coupling pin selectively cooperating with a plurality of openings formed in the needle shaft, which releasable coupling pin, when released, allows the needle shaft to reciprocate in the sheath assembly; and a movable holding pin, cooperating with a groove formed in the needle shaft to hold the needle shaft and the needle point in a withdrawn position within the sheath assembly.

* * * * *